United States Patent [19]
Sauer

[11] Patent Number: 5,957,907
[45] Date of Patent: Sep. 28, 1999

[54] ABSORBENT ARTICLE HAVING A CLOSE TO THE BODY LINER

[75] Inventor: Barbara Oakley Sauer, Fremont, Wis.

[73] Assignee: Kimberly-Clark Worldwide, Inc., Neenah, Wis.

[21] Appl. No.: 08/910,321

[22] Filed: Aug. 13, 1997

[51] Int. Cl.[6] .............................. A61F 13/15; A61F 13/20
[52] U.S. Cl. .................................. 604/385.2; 604/385.1; 604/378
[58] Field of Search ..................................... 604/358, 378, 604/385.1, 385.2, 386–387, 393, 394, 396

[56] References Cited

U.S. PATENT DOCUMENTS

| | | | |
|---|---|---|---|
| 4,892,536 | 1/1990 | DesMarais et al. | 604/385.2 |
| 4,990,147 | 2/1991 | Freeland | 604/385.2 |
| 5,037,416 | 8/1991 | Allen | 604/385.1 |
| 5,062,840 | 11/1991 | Holt et al. | 604/385.1 |
| 5,134,007 | 7/1992 | Reising et al. | 604/378 |
| 5,269,775 | 12/1993 | Freeland et al. | 604/385.1 |
| 5,318,554 | 6/1994 | Young et al. | 604/378 |
| 5,624,422 | 4/1997 | Allen | 604/385.1 |
| 5,779,690 | 7/1998 | Gustafsson | 604/385.1 |
| 5,817,086 | 10/1998 | Kling | 604/395 |

FOREIGN PATENT DOCUMENTS

| | | | |
|---|---|---|---|
| 0626160 | 11/1994 | European Pat. Off. | 604/385.2 |
| 9516419 | 6/1995 | WIPO | 604/385.1 |
| 9620674 | 7/1996 | WIPO | 604/385.1 |
| WO 97/49366 A1 | 12/1997 | WIPO . | |
| WO 98/25563 A1 | 6/1998 | WIPO . | |

*Primary Examiner*—Mark O. Polutta
*Attorney, Agent, or Firm*—Jeffrey B. Curtin

[57] ABSTRACT

An absorbent article includes a close fitting bodyside liner having an opening therein. The opening defines a front end edge, a rear end edge, and a pair of laterally opposed side edges. The article also includes a pair of elastic members which extend longitudinally beyond at least one of the end edges of the opening in a laterally divergent direction. The elastic members may also extend at least partially along the side edges of the opening. The elastic members are configured to maintain the edges of the opening in contact with the wearer's buttocks and align the opening with the wearer's anal opening in use. The article may further include a liquid management material located on the bodyside liner in the front waist section to absorb or contain liquid exudates.

30 Claims, 3 Drawing Sheets

ABSORBENT ARTICLE HAVING A CLOSE TO THE BODY LINER

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to collect and contain fecal material and avoid leakage.

2. Description of the Related Art

Conventional absorbent articles, such as disposable diapers, employ absorbent materials located between a liquid pervious bodyside liner and a liquid impermeable outer cover to absorb body exudates. Such conventional absorbent articles have also typically included elasticized waistbands and leg cuffs to help reduce the leakage of body exudates.

However, many of such conventional absorbent articles have not been completely satisfactory. In particular, many of such conventional absorbent articles have not completely contained or isolated the body exudates within the article during use thereby undesirably resulting in body exudates contacting the skin of the wearer. Such contact has been known to result in irritation of the skin of the wearer. For example, a common problem associated with the care of infants has been diaper rash which is at least partially caused by the contact of body exudates, including both fecal material and urine, with the infant's skin. As a result, there remains a need to better isolate body exudates from the skin of the wearer to reduce the level of skin irritation.

Moreover, the inability of many conventional absorbent articles to contain body exudates within the article has undesirably resulted in leakage which has soiled the clothes of the wearer. The leakage problem has been particularly evident in the leg and waist regions of such absorbent articles when runny or watery fecal material has been excreted by the wearer during use. Typically, the runny or watery fecal material has been forced laterally and longitudinally outwards from the crotch of the article towards the leg and waist regions of the article due to the forces exerted by the wearer. Such problems are magnified when the wearer is particularly active and continually exerts pressure on the crotch area of the article. The leakage problem has also occurred because such fecal material, which has an affinity for the skin, has come in contact with the skin and traveled along the skin of the wearer through the leg and waist openings. Thus, in many conventional absorbent articles, body exudates have not been sufficiently contained and controlled within the absorbent article.

Some conventional absorbent articles have included elasticized components and containment or barrier flaps at the leg and waist regions of the article to reduce such leaks. However, such elasticized components and containment flaps have not always isolated the body exudates from the skin of the wearer and eliminated leakage from the leg and waist regions of such articles. For example, exudates such as runny fecal material have remained on and been transferred along the skin of the wearer until they escape through small openings between the containment flaps and the body of the wearer. Such openings between the body of the wearer and the containment flaps have been caused by improper fit of the article about the wearer and the movements of the wearer during use.

Other conventional absorbent articles have included bodyside liners with holes therein which are configured to allow fecal exudates from the wearer to pass through the liner. However, such bodyside liners with holes therein have not been completely satisfactory. For example, frequently the hole in the bodyside liner of such conventional articles does not maintain correct alignment with the anal opening of the wearer to receive the fecal exudates. Such a problem has been particularly severe when the wearer is active. As a result, fecal exudates may not go through the hole and may instead undesirably remain in contact with the skin of the wearer on the bodyfacing surface of the bodyside liner. In an effort to solve this problem, several conventional absorbent articles have included larger holes in their liners to ensure that the hole is in position to receive the exudates. However, as the size of the hole increases, the amount of fecal exudates which remain in contact with the skin of the wearer also undesirably increases.

As a result, although such leg elastics, containment flaps and bodyside liners have improved the performance of such articles, there remains a need to further reduce the number of leaks of body exudates from the leg and waist regions of such absorbent articles. There further remains a need to better isolate the fecal exudates between the bodyside liner and the absorbent body of the articles to reduce the contact between the skin of the wearer and the fecal exudates during use for improved skin wellness.

SUMMARY OF THE INVENTION

In response to the difficulties and problems discussed above, a new disposable absorbent article which includes an improved close to the body liner for isolating and containing body exudates has been discovered.

In one aspect, the present invention relates to a disposable absorbent article which includes a bodyside liner having an opening therein. The opening defines a front end edge, a rear end edge, and a pair of laterally opposed side edges. The article also includes a pair of elastic members which extend at least partially along the side edges of the opening and which extend longitudinally beyond at least one of the end edges of the opening in a laterally divergent direction. The elastic members are configured to maintain the edges of the opening in contact with a wearer's buttocks in use. In a particular embodiment, the side edges of the opening in the bodyside liner diverge laterally outward in the rear waist section of the absorbent article.

In another aspect, the present invention relates to a disposable absorbent article having a front waist section, a rear waist section, and an intermediate section which interconnects the front and rear waist sections. Each of the waist sections defines a pair of laterally opposed ear portions. The article includes an outer cover, a bodyside liner which is connected in superposed relation to the outer cover and an absorbent body located between the outer cover and the bodyside liner. The bodyside liner defines an opening therein for receiving fecal exudates. The opening defines a front end edge, a rear end edge and a pair of laterally opposed side edges. The article also includes a pair of elastic members which extend longitudinally beyond the front end edge of the opening in a laterally divergent direction into the opposed ear portions of the front waist section to maintain the edges of the opening in contact with the wearer's buttocks in use.

In yet another aspect, the present invention relates to a disposable absorbent article having a front waist section, a rear waist section, and an intermediate section which interconnects the front and rear waist sections. The article includes an outer cover, a bodyside liner which is connected in superposed relation to the outer cover and an absorbent body located between the outer cover and the bodyside liner. The bodyside liner defines an opening therein for receiving fecal exudates and the opening defines a front end edge, a rear end edge and a pair of laterally opposed side edges. The article also includes a pair of elastic members which extend at least partially along the side edges of the opening to maintain the edges of the opening in contact with the wearer's buttocks in use. The article further includes a liquid management layer located on the bodyside liner in the front waist section of the absorbent article which is configured to efficiently contain liquid exudates.

The various aspects of the present invention can advantageously provide an absorbent article which effectively isolates, absorbs and contains body exudates. In particular, the absorbent article of the present invention includes a close to the body liner which reduces the amount of contact between body exudates and the wearer's skin and reduces the amount of leakage of such exudates from the leg and waist regions of the article. As a result, the absorbent articles of the various aspects of the present invention have reduced levels of skin irritation and leakage when compared to conventional absorbent articles which results in improved consumer preference.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
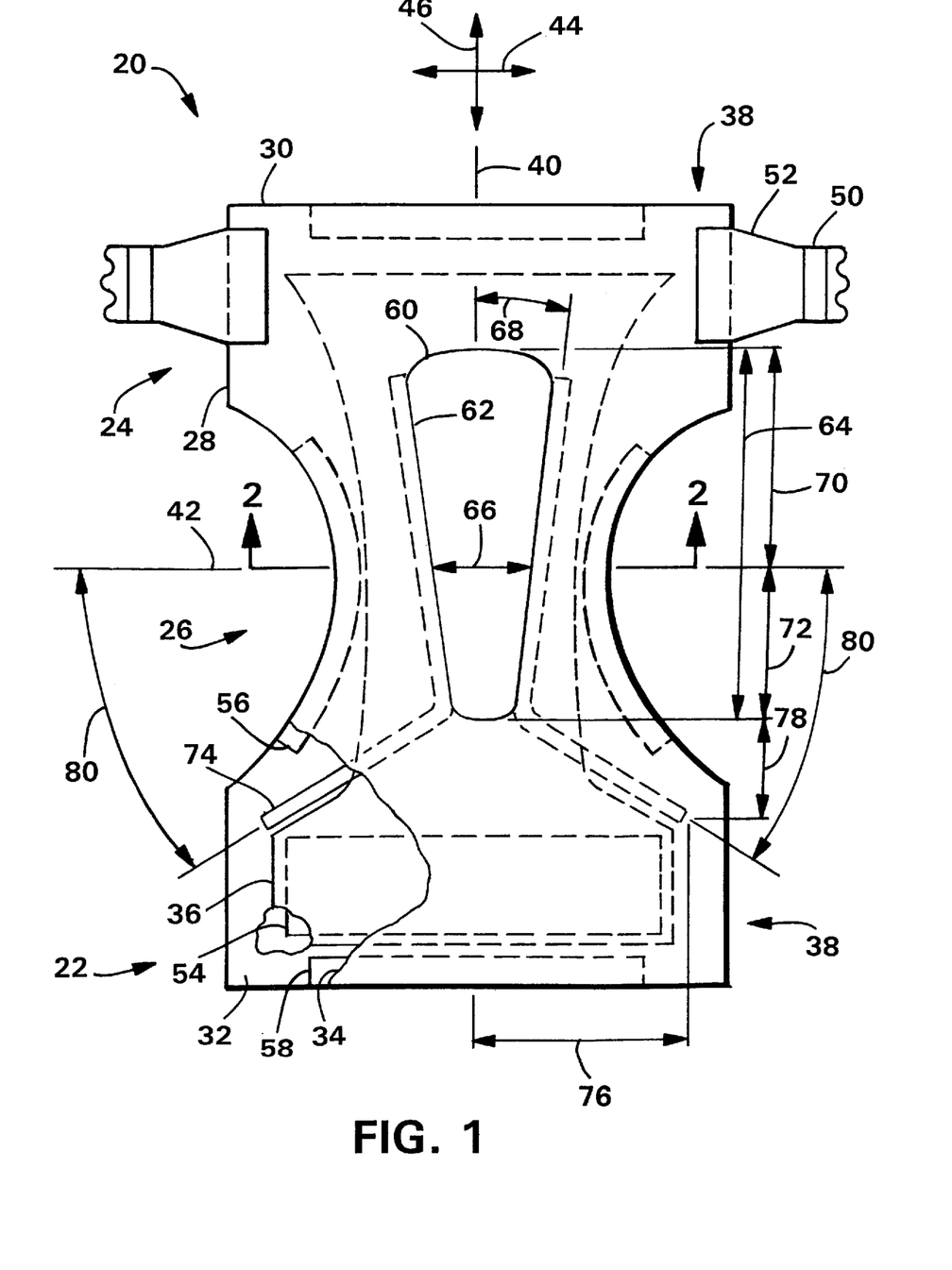
FIG. 1 representatively shows a partially cut away, top plan view of an absorbent article according to one embodiment of the invention.
Figure 2:
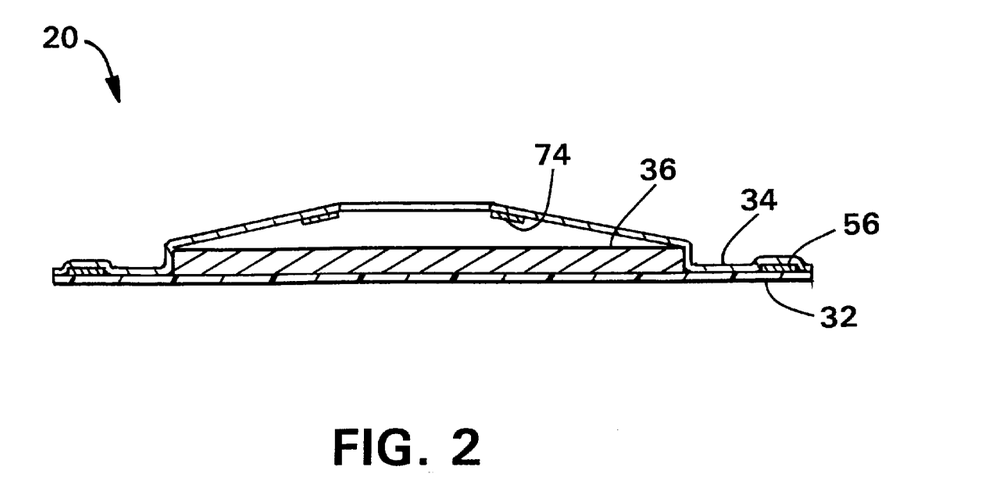
FIG. 2 representatively shows a sectional view of the absorbent article of FIG. 1 taken along line 2—2.

With reference to FIGS. 1 and 2, an integral absorbent garment article, such as disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear. The diaper 20 further defines a longitudinal centerline 40, a lateral centerline 42, a lateral direction 44 and a longitudinal direction 46.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable bodyside liner 34 positioned in facing relation with the outer cover 32, and an absorbent body 36, such as an absorbent pad, which is located between the outer cover and the bodyside liner. Marginal portions of the diaper 20, such as marginal sections of the outer cover 32, may extend past the terminal edges of the absorbent body 36. In the illustrated embodiment, for example, the outer cover 32 extends outwardly beyond the terminal marginal edges of the absorbent body 36 to form side margins and end margins of the diaper 20. The bodyside liner 34 is generally coextensive with the outer cover 32 but may optionally cover an area which is larger or smaller than the area of the outer cover 32, as desired.

The diaper 20 may be of various suitable shapes. For example, the diaper may have an overall rectangular shape, T-shape or an approximately hour-glass shape. In the shown embodiment, the diaper 20 has an overall hourglass or I-shape. In such a configuration, the diaper also defines a pair of laterally opposed ear portions 38 in both the front and rear waist sections 22 and 24 of the diaper. The ear portions 38 are those portions of the diaper 20 which extend laterally beyond the narrowest portion of the diaper 20 which is generally along the lateral centerline 42 in the intermediate section 26 of the diaper 20.

The diaper 20, as representatively illustrated in FIG. 1, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 44 of the diaper 20. The diaper 20 may also include an attachment panel 54 to which the fasteners 50 are intended to releasably engage to secure the diaper 20 about the waist of the wearer. For example, in one embodiment, the fasteners 50 may include hook type fasteners and the attachment panel 54 may include a complimentary loop type fastener to which the hook type fasteners are intended to releasably engage. Materials suitable for the fasteners 50 and attachment panel 54 are well known to those skilled in the art. Alternatively, the fasteners 50 may be configured to releasably engage the outer cover 32.

To provide improved fit and to help reduce leakage of body exudates from the diaper 20, the side margins and end margins of the diaper may be elasticized with suitable elastic members, such as leg elastic members 56 and waist elastic members 58. For example, the leg elastic members 56 may include single or multiple strands of elastic or elastomeric composites which are constructed to operably gather and shirr the side margins of the diaper 20 to provide elasticized leg bands which can closely fit around the legs of the wearer to reduce leakage and provide improved comfort and appearance. Similarly, the waist elastic members 58 can be employed to elasticize the end margins of the diaper 20 to provide elasticized waistbands. The waist elastics are configured to operably gather and shirr the waistband sections to provide a resilient, comfortably close fit around the waist of the wearer.

The elastic members 56 and 58 are secured to the diaper 20 in an elastically contractible condition so that in a normal under strain configuration, the elastic members effectively contract against the diaper 20. For example, the elastic members 56 and 58 may be elongated and secured to the diaper 20 while the diaper is in an uncontracted condition. In FIG. 1, the elastic members 56 and 58 are illustrated in their uncontracted, stretched condition for the purpose of clarity. Alternatively, the diaper 20 may include a pair of separate, elasticized and gathered leg gussets (not shown) which are attached to the diaper along the side margins in at least the intermediate section 26 of the diaper 20 to provide elasticized leg cuffs. Such leg gussets may be configured to extend beyond and bridge across the respective concave portion of the side margins of the diaper 20.

Figure 3:
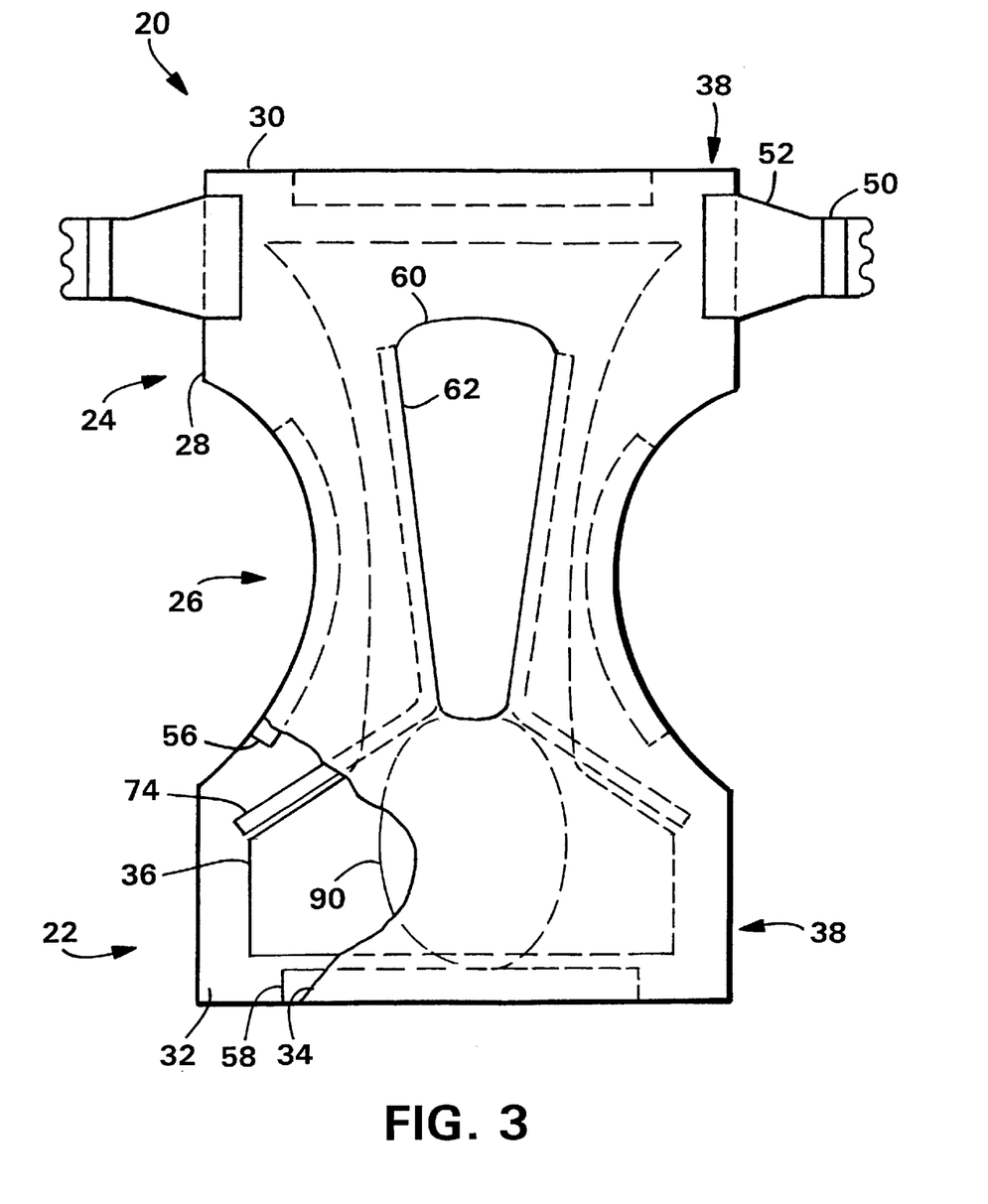
FIG. 3 representatively shows a partially cut away, top plan view of an absorbent article according to another embodiment of the invention.

As representatively illustrated in FIG. 3, the diaper 20 may further include a liquid management layer 90 positioned on the bodyside liner 34 in the front waist section 22 of the diaper 20. The liquid management layer 90 is configured to contain liquid exudates or hold and distribute the liquid exudates to the absorbent body 36. The liquid management layer 90 can prevent the liquid exudates from pooling and collecting on the portion of the bodyside liner 34 positioned against the wearer's skin, thereby reducing the level of skin hydration. The liquid management layer 90 may have any desired shape and configuration and may cover the entire bodyside liner 34 in the front waist section 22 of the diaper 20 or only a portion thereof. In the illustrated embodiment, the liquid management layer 90 defines an oval shape and defines an area of from about 10 to about 150 square centimeters.

Various woven and nonwoven fabrics can be used to construct the liquid management layer 90. For example, the liquid management layer 90 may comprise a layer composed of a meltblown or spunbonded web of polyolefin fibers. The liquid management layer 90 may otherwise comprise a bonded carded web or an airlaid web of natural or synthetic fibers. The liquid management layer 90 may be composed of a substantially hydrophobic material which may or may not be treated to impart a desired level of wettability and hydrophilicity. Alternatively, other suitable materials such as those described below as being suitable for the absorbent body 36 of the diaper 20 of the present invention may be used to provide the liquid management layer 90.

The diaper 20 may further include a pair of longitudinally extending, compression resistant containment barriers (not illustrated) located along the side edges 28 of the diaper 20 at least in the intermediate section of the diaper 20. Such containment barriers are configured to reduce the lateral flow of fecal exudates out of the leg regions of the diaper 20 and provide a void space between the buttocks of the wearer and the absorbent portion of the diaper 20 during use. The void space is configured to contain body exudates and, in particular, fecal exudates until they can be absorbed or desorbed by the absorbent body 36 of the diaper 20. The diaper 20 may further include at least one containment dam (not illustrated) which is configured to inhibit the longitudinal flow of fecal exudates into regions of the diaper 20 such as the rear waist section 24 to more effectively contain such material within the diaper 20. Suitable constructions of such containment barriers and containment dams are set forth in commonly assigned U.S. patent application Ser. No. 08/763,960 entitled "ABSORBENT ARTICLES HAVING THREE DIMENSIONAL LONGITUDINAL CONTAINMENT DAMS", filed Dec. 5, 1996, in the name of B. O. Sauer and U.S. patent application Ser. No. 08/706,581 entitled "ABSORBENT ARTICLES HAVING A CONTAINMENT DAM", filed Sep. 5, 1996, in the name of B. O. Sauer.

Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; and U.S. Pat. No. 5,509,915 issued Apr. 23, 1996, to Hanson et al., the disclosures of which are herein incorporated by reference to the extent they are consistent herewith. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the bodyside liner 34 and outer cover 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the fasteners 50 and the elastic members 56 and 58, may be assembled into the diaper 20 article by employing the above-identified attachment mechanisms.

The outer cover 32 of the diaper 20, as representatively illustrated in FIG. 1, may suitably be composed of a material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent body 36. Still further, the outer cover 32 may optionally be composed of a micro-porous "breathable" material which permits vapors to escape from the absorbent body 36 while still preventing liquid exudates from passing through the outer cover 32. The outer cover 32 can also be embossed or otherwise provided with a matte finish to provide a more aesthetically pleasing appearance.

The bodyside liner 34, as representatively illustrated in FIG. 1, suitably presents a bodyfacing surface which is compliant, soft feeling, and nonirritating to the wearer's skin. The bodyside liner 34 in the different aspects of the present invention is configured to remain in close contact with the wearer's buttocks in use. Further, the bodyside liner 34 may be less hydrophilic than the absorbent body 36, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 34 is suitably employed to help isolate the wearer's skin from liquids held in the absorbent body 36.

Various woven and nonwoven fabrics can be used for the bodyside liner 34. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire bodyside liner 34 or may be selectively applied to particular sections of the bodyside liner 34, such as the medial section along the longitudinal centerline of the diaper, to provide greater wettability of such sections.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet material located on the opposite side of the fibrous mass.

The bodyside liner 34 of the diaper 20 of the present invention, as representatively illustrated in FIG. 1, also includes an opening 60 therein which is configured to receive fecal exudates and isolate at least a portion of such exudates from the skin of the wearer. The opening 60 is located such that the fecal exudates pass through the opening 60 in the bodyside liner 34 and into the void space between the bodyside liner 34 and absorbent body 36 of the diaper 20 during use. At least a portion of the fecal exudates which are contained in the void space may then be absorbed or desorbed by the absorbent body 36.

Desirably, the opening 60 in the bodyside liner 34 is located such that it is in alignment with the wearer's anal opening in use. For example, the opening 60 in the bodyside liner 34 is located in the target zone of the diaper 20. As used herein, the term "target zone" refers to that portion of the diaper 20 which is configured to directly receive the insult of fecal exudates from the wearer and generally is located in the crotch portion of the diaper 20. In particular, the target zone may extend from about 5 to about 10 centimeters in length with about one third of it's length extending longitudinally from the lateral centerline 42 of the diaper towards the front waist section 22 of the diaper 20 and the remainder extending longitudinally towards the rear waist section 24 of the diaper 20.

The opening 60 in the bodyside liner 34 generally defines a front end edge, a rear end edge and a pair of laterally opposed side edges 62. The front and rear end edges of the opening 60 are generally the longitudinally opposed end edges of the opening 60 located adjacent or in the front and rear waist sections 22 and 24 of the diaper 20, respectively. The opening 60 in the bodyside liner 34 further defines a length 64 in the longitudinal direction 46 and a width 66 in the lateral direction 44. As used herein, the length 64 and width 66 of the opening 60 refer to the length and width of the opening 60 along the longitudinal centerline 40 and lateral centerline 42 of the diaper 20, respectively.

The length 64 and width 66 of the opening 60 must be sufficient to allow fecal exudates to pass through into the void space created between the bodyside liner 34 and absorbent body 36. However, the size of the opening 60 must not be too large such that the bodyside liner 34 surrounding the opening 60 can effectively isolate or prevent at least a portion of the fecal exudates which pass through the opening 60 into the void space from remaining in contact with the skin of the wearer during use. Thus, the dimensions of the opening 60 may be controlled to provide both improved containment of body exudates and improved skin wellness of the wearer.

For example, on a diaper article intended to be worn by a medium sized infant, the opening may define a length 64 along the longitudinal centerline 40 of the diaper 20 of no more than about 12.7 centimeters and desirably no more than about 10 centimeters and a width 66 as measured along the lateral centerline 42 of the diaper 20 of no more than about 7.5 centimeters and desirably from about 3.8 to about 6.3 centimeters. Desirably, the opening 60 defines a length 64 along the longitudinal centerline 40 which is no more than about 50 percent and more desirably no more than about 35 percent of the length of the diaper 20 as measured along the longitudinal centerline 40 of the diaper 20 and a width 66 which is no more than about 50 percent and more desirably no more than about 35 percent of the width of the diaper 20 as measured along the lateral centerline 42 of the diaper 20 for improved containment and isolation of the fecal exudates within the void space between the bodyside liner 34 and the absorbent body 36. The opening 60 may further define an open area of no more than about 150 square centimeters and desirably from about 20 to about 100 square centimeters for improved performance. representatively illustrated in FIG. 1, the opening 60 in the bodyside liner 34 is desirably located such that about one third or less of it's length 64 extends longitudinally from the lateral centerline 42 of the diaper 20 towards the front waist section 22 of the diaper 20 and the remainder extends longitudinally towards the rear waist section 24 of the diaper 20. Desirably, at least about 60 percent and more desirably from about 70 to about 80 percent of the length 64 of the opening 60 is located rearward of the lateral centerline 42 of the diaper 20 for improved performance. For example, on a diaper article intended to be worn by a medium sized infant, the opening may define a length 70 rearward of the lateral centerline 42 of the diaper 20 of from about 4.0 to about 16.0 centimeters and desirably from about 5.0 to about 10.0 centimeters and a length 72 on the front waist side of the lateral centerline 42 of the diaper 20 of from about 0.25 to about 5.0 centimeters and desirably from about 1.0 to about 3.0 centimeters. Such a configuration provides improved alignment between the opening 60 in the bodyside liner 34 and the wearer's anal opening. As used herein, the term "rearward" relates to the direction extending from the lateral centerline 42 towards the rear waist section 24 of the diaper 20.

The opening 60 may have any shape which is capable of receiving the fecal exudates. Suitable shapes include circular, oval, elliptical, square, rectangular, triangular and the like. In a particular embodiment as representatively illustrated in FIG. 1, the opening 60 defines a triangular shape with the laterally opposed side edges 62 of the opening 60 diverging from each other laterally outward in the rear waist section 24 of the diaper 20. Such a configuration has been found to better fit the buttocks of the wearer which may provide improved reception and containment of the fecal exudates. This is particularly true since the anal opening of the wearer is generally located rearward of the lateral centerline of the article being worn. Thus, it is desirable that the opening 60 in the bodyside liner 34 be sized and shaped to ensure it is in position to receive fecal exudates from the wearer's anal opening.

In this regard, the side edges 62 of the opening 60 desirably diverge laterally outward as they extend from the lateral centerline 42 of the diaper 20 towards the rear waist section 24 of the diaper 20 as representatively illustrated in FIG. 1. In such a configuration, the side edges 62 of the opening 60 define an angle of divergence 68 with respect to the longitudinal centerline 40 of the diaper 20. In a particular embodiment, the side edges 62 define an angel of divergence 68 of from about 5 to about 45 degrees and desirably from about 10 to about 30 degrees for improved reception and containment of fecal exudates.

The size of the portion of the opening 60 in the bodyside liner 34 which extends towards the front waist section 22 from the lateral centerline 42 of the diaper 20 need not be as large. Typically, the portion of the opening 60 extending from the lateral centerline 42 towards the front waist section 22 is available to receive any fecal exudates which may pass from the anal opening along the gluteal groove between the buttocks of the wearer. Thus, as illustrated in FIG. 1, the side edges 62 of the opening 60 may further converge laterally inward as they extend from the lateral centerline 42 of the diaper 20 towards the front waist section 22 of the diaper 20 for improved isolation of the fecal exudates in the void space between the bodyside liner 34 and the absorbent body 36 of the diaper 20.

The diaper 20 of the different aspects of the present invention further includes at least one elastic member 74 attached to the bodyside liner 34. The elastic member 74 is configured to ensure that the opening 60 in the bodyside liner 34 remains aligned to receive fecal exudates from the wearer's anal opening particularly during active periods. The elastic member 74 further maintains the opening 60 in contact with the wearers body to reduce the amount of exudates on the bodyfacing surface of the bodyside liner 34 thereby reducing the level of skin irritation. The elastic members 74 also gathers and shirrs the bodyside liner 34 which desirably provides the void space between the bodyside liner 34 and the absorbent body 36 of the diaper 20 for containing the fecal exudates. As discussed above, once the fecal exudates pass through the opening 60 in the bodyside liner into such void space, they can then be absorbed or desorbed by the absorbent body 36.

The elastic member 74 can comprise any suitable elastic material such as, for example, one or more strands of individual elastic material. For example, a suitable elastic strand may be composed of a 470 decitex LYCRA elastomer which is available from E. I. DuPont de Nemours. The elastic member 74 desirably is connected to the bodyside liner 34 in an elastically contractible condition such that the contraction of the elastic member 74 contracts and gathers the bodyside liner 34 for improved fit and performance. In FIG. 1, the elastic members 74 are illustrated in their uncontracted, stretched condition for the purpose of clarity.

In a particular embodiment as representatively illustrated in FIG. 1, the diaper 20 includes a pair of laterally opposed elastic members 74 which extend longitudinally beyond at least one of the end edges of the opening in a laterally divergent direction. In such a configuration, the elastic members 74 are configured to better maintain the opening 60 in the bodyside liner 34 in proper alignment with the wearer's anal opening to receive the fecal exudates. Such diverging elastics are further configured to fit in the creases or seams extending between the legs, buttocks and upper torso of the wearer's body to provide improved fit of the bodyside liner 34 in such seams. Thus, since such diverging elastic members 74 can maintain improved alignment of the opening 60 with respect to the wearers body, the size of the opening 60 in the bodyside liner 34 may be reduced compared to conventional absorbent articles having liners with holes therein. As discussed above, the smaller size of the opening 60 in the bodyside liner 34 of the present invention can desirably reduce the amount of contact between the fecal exudates which pass through the opening 60 and the skin of the wearer thereby resulting in improved skin wellness.

As representatively illustrated, the elastic members 74 extend longitudinally beyond the end edge of the opening 60 in a laterally divergent direction which defines an angle of divergence 80 with respect to the lateral centerline 42 of the diaper 20. Desirably, the elastic members 74 extend towards the corners of the diaper 20 defined by the intersection of the side edges 28 and end edges 30 of the diaper 20. To provide the improved fit and alignment discussed above, the angle of divergence 80 of the elastic members as they extend beyond the end edge of the opening 60 is from about 20 to about 70 degrees and desirably from about 30 to about 45 degrees.

Desirably, the elastic members 74 extend longitudinally and laterally outward into the laterally opposed ear portions 38 of the diaper 20 in one of the waist sections of the diaper 20 to maintain the opening 60 in contact and proper alignment with the wearer's body. In such a configuration, the ends of the elastic members 74 may be adjacent or in alignment with the fasteners 50 or fastening panel 54 such that the fastening of the diaper about the waist of the wearer exerts forces on the elastic members 74 to maintain the opening 60 in proper alignment for receiving fecal exudates.

Such forces exerted on the elastic members 74 by the fastening of the diaper 20 about the wearer also assist in maintaining the bodyside liner 34 in contact with the wearer's skin. In particular, such a configuration of the elastic members 74 maintains the bodyside liner 34 in contact with the upper thigh and stomach of the wearer for improved performance. For example, in the illustrated embodiment, the elastic members 74 extend longitudinally beyond the front end edge of the opening 60 into the ear portions 38 and adjacent or near the fastening panel 54 in the front waist section 22 of the diaper 20.

As illustrated in FIG. 1, the portion of the elastic members 74 which extend longitudinally beyond the opening 60 also extend laterally outward from the longitudinal centerline 40 of the diaper 20 a distance 76. Desirably, the elastic members 74 extend laterally outward a distance 76 of at least about 2.0 centimeters to ensure proper alignment of the opening 60 with respect to the wearer. The elastic members 74 further extend longitudinally beyond the end edge of the opening 60 a distance 78. For improved fit and alignment of the opening to the wearer's body, the elastic members 74 desirably extend longitudinally beyond the end edge of the opening a distance 78 of at least about 5 percent of a total length of the diaper 20. For example, in a diaper 20 intended for use by a medium sized infant, the elastic members 74 desirably extend longitudinally beyond the end edge of the opening a distance 78 of at least about 5.0 centimeters.

As illustrated in FIG. 1, the elastic members 74 on the bodyside liner 34 may further extend along at least a portion of a length of both of the laterally opposed side edges 62 of the opening 60 in the bodyside liner 34. In such a configuration, the elastic members 74 can assist in providing a close conforming fit between the bodyside liner 34 and the buttocks of the wearer which results in improved alignment of the opening 60 over the anus of the wearer to better receive fecal exudates. The elastic members 74 are also configured to provide a seal with the wearer's buttock to help reduce leaks along the side edges 62 of the opening 60 in the bodyside liner 34 of the diaper 20 by preventing the lateral flow of fecal exudates. Desirably, the elastic members 74 are configured to maintain the side edges 62 of the opening 60 in contact with the wearers buttocks during use to provide improved resistance to the explosive lateral flow of fecal exudates which may occur due to the compressive forces exerted by the wearer while sitting.

In a particular embodiment as illustrated in FIG. 1, it is desirable that the elastic members 74 do not extend along or adjacent the front end edge of the opening 60 in the front waist section 22 of the diaper 20 to reduce irritation of the wearers genitals and provide improve fit and comfort.

As a result, the different aspects of the present invention can advantageously provide an absorbent article which effectively isolates, absorbs and contains body exudates. The absorbent article includes a close to the body liner which is configured to reduce the amount of contact between such body exudates and the wearer's skin and reduce the amount of leakage of such body exudates from the leg and waist regions of the article. In particular, the absorbent article includes a bodyside liner having an opening therein which has sufficient size to allow fecal exudates to pass through while not being too large to allow excessive contact between the fecal exudates and the wearer's skin. Moreover, the absorbent article includes at least one elastic member attached to the bodyside liner to maintain proper alignment of the opening with the wearer's anus and maintain contact between the liner and the wearer's body. As a result, the absorbent articles of the various aspects of the present invention have reduced levels of skin irritation and leakage when compared to conventional absorbent articles which results in improved consumer acceptance.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. A disposable absorbent article which includes an absorbent superposed on a bodyside liner and at least one pair of laterally opposed ear portions which extend laterally beyond a narrowest portion of said absorbent article, said bodyside liner having an opening therein which defines a front end edge, a rear end edge, and a pair of laterally opposed side edges which diverge laterally outward in a rear waist section of said article, wherein said article comprises a pair of elastic members which extend at least partially along said side edges of said opening and which extend longitudinally beyond at least one of said end edges of said opening in a laterally divergent direction into said opposed ear portions of said absorbent article to maintain said edges of said opening in contact with a wearer's buttocks in use.

2. The absorbent article according to claim 1 wherein said opening in said bodyside liner defines a length of no more than about 50 percent of a length of said absorbent article.

3. The absorbent article according to claim 1 wherein said opening in said bodyside liner defines a length of no more than about 30 percent of a length of said absorbent article.

4. The absorbent article according to claim 1 and wherein at least about 60 percent of a length of said opening is located rearward of a lateral centerline of said absorbent article.

5. The absorbent article according to claim 1 wherein said opening in said bodyside liner defines a width along a lateral centerline of said absorbent article of no more than about 50 percent of a width of said absorbent article along said lateral centerline.

6. The absorbent article according to claim 1 wherein said opening defines an area of no more than about 150 square centimeters.

7. The absorbent article according to claim 1 wherein said side edges of said opening in said bodyside liner define an angle of divergence with respect to a longitudinal centerline of said absorbent article of from about 5 to about 45 degrees.

8. The absorbent article according to claim 1 wherein said side edges of said opening in said bodyside liner converge laterally inward in a front waist section of said absorbent article.

9. The absorbent article according to claim 1 wherein said elastic members extend longitudinally beyond said front end edge of said opening in a laterally divergent direction.

10. The absorbent article according to claim 1 wherein said elastic members extend longitudinally beyond said end edge of said opening a distance in a longitudinal direction of at least about 5 percent of a length of said absorbent article.

11. The absorbent article according to claim 1 wherein said elastic members which extend longitudinally beyond said end edge of said opening further extend outward in a lateral direction measured from a longitudinal centerline of said absorbent article a distance of at least about 2.0 centimeters.

12. The absorbent article according to claim 1 wherein said elastic members extend longitudinally beyond said end edge of said opening at an angle of divergence with respect to a lateral centerline of said absorbent article of from about 20 to about 70 degrees.

13. The absorbent article according to claim 1 wherein said elastic members extend longitudinally beyond said end edge of said opening at an angle of divergence with respect to a lateral centerline of said absorbent article of from about 30 to about 45 degrees.

14. The absorbent article according to claim 1 wherein each of said elastic members includes a plurality of elastic strands.

15. A disposable absorbent article having a front waist section, a rear waist section, an intermediate section which interconnects said front and rear waist sections, and a pair of laterally opposed side margins wherein each of said waist sections defines a pair of laterally opposed ear portions which extend laterally beyond a narrowest portion of said absorbent article, said article comprising:

a) an outer cover;

b) a bodyside liner which is connected in superposed relation to said outer cover and which defines an opening therein for receiving fecal exudates wherein said opening defines a front end edge, a rear end edge and a pair of laterally opposed side edges;

c) an absorbent body which is located between said bodyside liner and said outer cover;

d) a first pair of discrete elastic members located along said opposed side margins of said article to provide elasticized leg bands; and e) a second pair of discrete elastic members located laterally inward from said first pair of discrete elastic members and at least partially along said side edges of said opening wherein said second pair of elastic members extend longitudinally beyond said front end edge of said opening in a laterally divergent direction into said opposed ear portions of said front waist section of said absorbent article to maintain said edges of said opening in contact with a wearer's buttocks in use.

16. The absorbent article according to claim 15 wherein said opening in said bodyside liner defines a length of no more than about 50 percent of a length of said absorbent article.

17. The absorbent article according to claim 15 wherein said opening in said bodyside liner defines a length of no more than about 30 percent of a length of said absorbent article.

18. The absorbent article according to claim 15 and wherein at least about 60 percent of a length of said opening is located rearward of a lateral centerline of said absorbent article.

19. The absorbent article according to claim 15 wherein said side edges of said opening in said bodyside liner diverge laterally outward in said rear waist section of said absorbent article.

20. The absorbent article according to claim 15 wherein said side edges of said opening in said bodyside liner define an angle of divergence with respect to a longitudinal centerline of said absorbent article of from about 5 to about 45 degrees.

21. The absorbent article according to claim 15 wherein said elastic members extend longitudinally beyond said front end edge of said opening a distance in a longitudinal direction of at least about 5 percent of a length of said absorbent article.

22. The absorbent article according to claim 15 wherein said elastic members extend longitudinally beyond said front end edge of said opening at an angle of divergence with respect to a lateral centerline of said absorbent article of from about 20 to about 70 degrees.

23. The absorbent article according to claim 15 wherein said elastic members extend longitudinally beyond said end edge of said opening at an angle of divergence with respect to a lateral centerline of said absorbent article of from about 30 to about 45 degrees.

24. A disposable absorbent article having a front waist section, a rear waist section, an intermediate section which interconnects said front and rear waist sections, and a pair of laterally opposed side margins wherein each of said waist sections defines a pair of laterally opposed ear portions which extend laterally beyond a narrowest portion of said absorbent article, said article comprising:

a) an outer cover;
   b) a bodyside liner which is connected in superposed relation to said outer cover and which defines an opening therein for receiving fecal exudates wherein said opening defines a front end edge, a rear end edge and a pair of laterally opposed side edges;
   c) an absorbent body which is located between said bodyside liner and said outer cover;
   d) a first pair of discrete elastic members located along said opposed side margins of said article to provide elasticized leg bands;
   e) a second pair of discrete elastic members located laterally inward from said first pair of discrete elastic members and at least partially along said side edges of said opening, wherein said elastic members extend longitudinally beyond at least one of said end edges of said opening in a laterally divergent direction into said opposed ear portions of said absorbent article to maintain said edges of said opening in contact with a wearers buttocks in use; and
   f) a liquid management layer located on said bodyside liner in said front waist section of said absorbent article which is configured to contain and distribute liquid exudates.

25. The absorbent article according to claim 24 wherein said opening in said bodyside liner defines a length of no more than about 50 percent of a length of said absorbent article.

26. The absorbent article according to claim 24 and wherein at least about 60 percent of a length of said opening is located rearward of a lateral centerline of said absorbent article.

27. The absorbent article according to claim 24 wherein said side edges of said opening in said bodyside liner diverge laterally outward in said rear waist section of said absorbent article.

28. The absorbent article according to claim 24 wherein said side edges of said opening in said bodyside liner define an angle of divergence with respect to a longitudinal centerline of said absorbent article of from about 5 to about 45 degrees.

29. The absorbent article according to claim 24 wherein said elastic members further extend longitudinally beyond said front end edge of said opening in a laterally divergent direction.

30. The absorbent article according to claim 24 wherein said liquid management layer comprises a nonwoven material.

* * * * *